(12) United States Patent
Wenchell

(10) Patent No.: US 9,636,111 B2
(45) Date of Patent: May 2, 2017

(54) METHOD OF STAPLING TISSUES WITH A STAPLE ASSEMBLY

(75) Inventor: Thomas Wenchell, Durham, CT (US)

(73) Assignee: Covidien LP, Mansfield, MA (US)

( * ) Notice: Subject to any disclaimer, the term of this patent is extended or adjusted under 35 U.S.C. 154(b) by 770 days.

(21) Appl. No.: 12/598,064

(22) PCT Filed: May 5, 2008

(86) PCT No.: PCT/US2008/062635
§ 371 (c)(1),
(2), (4) Date: Oct. 29, 2009

(87) PCT Pub. No.: WO2008/137833
PCT Pub. Date: Nov. 13, 2008

(65) Prior Publication Data
US 2010/0137904 A1    Jun. 3, 2010

Related U.S. Application Data

(60) Provisional application No. 60/928,244, filed on May 7, 2007.

(51) Int. Cl.
| A61B 17/068 | (2006.01) |
| A61B 17/064 | (2006.01) |
| A61B 17/072 | (2006.01) |

(52) U.S. Cl.
CPC ...... *A61B 17/0643* (2013.01); *A61B 17/0686* (2013.01); *A61B 17/0644* (2013.01); *A61B 17/07292* (2013.01); *A61B 2017/07242* (2013.01); *A61B 2017/07264* (2013.01)

(58) Field of Classification Search
CPC . A61B 17/0643; A61B 17/068; A61B 17/072; A61B 17/064; A61B 17/0644; F16B 15/0015
USPC ........... 606/219–220; 411/457, 469, 478, 411/458–468; 227/175.1, 175.2–182.1; 24/28, 30.5, 35.5 L, 282, 21, 284, 23 EE, 24/20 EE, 20 H, 20 W, 33 A, 68 A, 68 E,
(Continued)

(56) References Cited

U.S. PATENT DOCUMENTS

| 1,756,670 A | 8/1926 | Treat |
| 3,258,012 A | 6/1966 | Nakayama et al. |
| 3,357,296 A * | 12/1967 | Lefever .................. 411/469 |

(Continued)

FOREIGN PATENT DOCUMENTS

| EP | 0 077 260 | 4/1983 |
| EP | 0129442 | 12/1984 |

(Continued)

OTHER PUBLICATIONS

European Search Report EP06016963.8-2318 dated Mar. 9, 2007.
(Continued)

*Primary Examiner* — Christopher L Templeton

(57) ABSTRACT

There is provided a variable size, uniform compression staple assembly for use in stapling differing thicknesses of tissues. The staple assembly includes a staple and a staple block for receipt of tissue penetrating tips of the staple. Upon assembly through tissue, the tissue penetrating tips of the staple lodge within the staple block to a depth inversely proportional to the thickness of the tissues being stapled. There is also disclosed an anvil configured for use with the staple assembly.

5 Claims, 4 Drawing Sheets

(58) Field of Classification Search
USPC .......... 24/131 C, 129 W; 248/74.1; 403/314; 385/60
See application file for complete search history.

(56) References Cited

U.S. PATENT DOCUMENTS

| | | | |
|---|---|---|---|
| 3,744,495 A * | 7/1973 | Johnson | 606/142 |
| 3,771,526 A | 11/1973 | Rudie | |
| 3,837,555 A | 9/1974 | Green | |
| 4,014,492 A | 3/1977 | Rothfuss | |
| 4,129,059 A * | 12/1978 | Van Eck | 411/475 |
| 4,179,583 A * | 12/1979 | Sergev | 174/21 R |
| 4,278,091 A | 7/1981 | Borzone | |
| 4,319,576 A | 3/1982 | Rothfuss | |
| 4,402,445 A * | 9/1983 | Green | 227/19 |
| 4,434,796 A * | 3/1984 | Karapetian et al. | 606/75 |
| 4,475,679 A | 10/1984 | Fleury, Jr. | |
| 4,527,437 A | 7/1985 | Wells | |
| 4,531,522 A | 7/1985 | Bedi et al. | |
| 4,532,927 A * | 8/1985 | Miksza, Jr. | 606/220 |
| 4,534,350 A * | 8/1985 | Golden et al. | 606/220 |
| 4,534,352 A * | 8/1985 | Korthoff | 606/220 |
| 4,548,202 A | 10/1985 | Duncan | |
| 4,573,469 A * | 3/1986 | Golden et al. | 606/220 |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,627,437 A * | 12/1986 | Bedi et al. | 606/220 |
| 4,671,280 A * | 6/1987 | Dorband et al. | 606/220 |
| 4,693,248 A * | 9/1987 | Failla | 606/220 |
| 4,741,336 A | 5/1988 | Failla et al. | |
| 4,767,044 A | 8/1988 | Green | |
| 4,809,695 A | 3/1989 | Gwathmey et al. | |
| 4,848,637 A | 7/1989 | Pruitt | |
| 4,881,545 A | 11/1989 | Isaacs et al. | |
| 4,889,119 A * | 12/1989 | Jamiolkowski et al. | 606/220 |
| 4,930,503 A | 6/1990 | Pruitt | |
| 4,941,623 A | 7/1990 | Pruitt | |
| 4,978,049 A | 12/1990 | Green | |
| 4,994,073 A * | 2/1991 | Green | 606/220 |
| 5,027,834 A | 7/1991 | Pruitt | |
| 5,108,422 A | 4/1992 | Green et al. | |
| 5,180,092 A | 1/1993 | Crainich | |
| 5,201,746 A | 4/1993 | Shichman | |
| 5,209,756 A | 5/1993 | Seedhom et al. | |
| 5,219,353 A | 6/1993 | Garvey, III et al. | |
| 5,240,163 A | 8/1993 | Stein et al. | |
| 5,282,829 A | 2/1994 | Hermes | |
| 5,342,396 A | 8/1994 | Cook | |
| 5,350,400 A | 9/1994 | Esposito et al. | |
| 5,352,229 A | 10/1994 | Goble et al. | |
| 5,425,489 A | 6/1995 | Shichman et al. | |
| 5,439,479 A * | 8/1995 | Shichman et al. | 606/220 |
| 5,441,193 A | 8/1995 | Gravener | |
| 5,452,836 A | 9/1995 | Huitema et al. | |
| 5,452,837 A | 9/1995 | Williamson, IV et al. | |
| 5,470,010 A | 11/1995 | Rothfuss et al. | |
| 5,480,089 A * | 1/1996 | Blewett | 227/175.1 |
| 5,484,095 A | 1/1996 | Green et al. | |
| 5,497,931 A | 3/1996 | Nakamura | |
| 5,501,693 A | 3/1996 | Gravener | |
| 5,509,920 A | 4/1996 | Phillips et al. | |
| 5,571,116 A | 11/1996 | Bolanos | |
| 5,571,285 A | 11/1996 | Chow et al. | |
| 5,584,856 A | 12/1996 | Jameel et al. | |
| 5,620,452 A | 4/1997 | Yoon | |
| 5,634,926 A | 6/1997 | Jobe | |
| 5,667,526 A | 9/1997 | Levin | |
| 5,667,527 A | 9/1997 | Cook | |
| 5,676,674 A | 10/1997 | Bolanos et al. | |
| 5,697,542 A | 12/1997 | Knodel et al. | |
| 5,709,680 A | 1/1998 | Yates et al. | |
| 5,741,268 A | 4/1998 | Schultz | |
| 5,810,822 A | 9/1998 | Mortier | |
| 5,865,361 A | 2/1999 | Milliman et al. | |
| 5,871,135 A | 2/1999 | Williamson, IV et al. | |
| 5,879,371 A | 3/1999 | Gardiner et al. | |
| 5,915,616 A | 6/1999 | Viola et al. | |
| 5,961,521 A | 10/1999 | Roger | |
| 5,964,394 A | 10/1999 | Robertson | |
| 6,083,242 A | 7/2000 | Cook | |
| 6,202,914 B1 | 3/2001 | Geiste et al. | |
| 6,273,897 B1 | 8/2001 | Dalessandro et al. | |
| 6,325,810 B1 | 12/2001 | Hamilton et al. | |
| 6,348,054 B1 | 2/2002 | Allen | |
| 6,488,196 B1 * | 12/2002 | Fenton, Jr. | 227/175.1 |
| 6,503,257 B2 * | 1/2003 | Grant et al. | 606/151 |
| 6,702,826 B2 | 3/2004 | Liddicoat et al. | |
| 6,706,057 B1 | 3/2004 | Bidoia et al. | |
| 6,786,382 B1 | 9/2004 | Hoffman | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,988,649 B2 | 1/2006 | Shelton, IV et al. | |
| 7,000,818 B2 | 2/2006 | Shelton, IV et al. | |
| 7,000,819 B2 | 2/2006 | Swayze et al. | |
| 7,001,411 B1 | 2/2006 | Dean | |
| 7,044,352 B2 | 5/2006 | Shelton, IV et al. | |
| 7,055,731 B2 | 6/2006 | Shelton, IV et al. | |
| 7,059,508 B2 | 6/2006 | Shelton, IV et al. | |
| 7,070,083 B2 | 7/2006 | Jankowski | |
| 7,398,907 B2 | 7/2008 | Racenet et al. | |
| 7,398,908 B2 | 7/2008 | Holsten et al. | |
| 7,455,676 B2 | 11/2008 | Holsten et al. | |
| 7,500,979 B2 | 3/2009 | Hueil et al. | |
| 7,547,312 B2 | 6/2009 | Bauman et al. | |
| 7,641,091 B2 | 1/2010 | Olson et al. | |
| 7,654,431 B2 | 2/2010 | Hueil et al. | |
| 7,722,610 B2 | 5/2010 | Viola et al. | |
| 7,794,475 B2 | 9/2010 | Hess et al. | |
| 2003/0149439 A1 * | 8/2003 | Wendlandt | A61B 17/0643 606/151 |
| 2004/0004105 A1 | 1/2004 | Jankowski | |
| 2004/0073222 A1 | 4/2004 | Koseki | |
| 2004/0093029 A1 | 5/2004 | Zubik et al. | |
| 2004/0232195 A1 | 11/2004 | Shelton et al. | |
| 2004/0232199 A1 | 11/2004 | Shelton et al. | |
| 2004/0247415 A1 | 12/2004 | Mangone, Jr. | |
| 2005/0006430 A1 | 1/2005 | Wales | |
| 2005/0006431 A1 | 1/2005 | Shelton et al. | |
| 2005/0006434 A1 | 1/2005 | Wales | |
| 2005/0023324 A1 | 2/2005 | Doll et al. | |
| 2005/0023325 A1 | 2/2005 | Gresham et al. | |
| 2005/0059997 A1 * | 3/2005 | Bauman | A61B 17/072 606/219 |
| 2005/0070925 A1 | 3/2005 | Shelton, IV et al. | |
| 2005/0070958 A1 | 3/2005 | Swayze et al. | |
| 2005/0173490 A1 | 8/2005 | Shelton, IV | |
| 2005/0178813 A1 | 8/2005 | Swayze et al. | |
| 2005/0187576 A1 | 8/2005 | Whitman et al. | |
| 2005/0245965 A1 * | 11/2005 | Orban, III | A61B 17/068 606/214 |
| 2005/0263562 A1 | 12/2005 | Shelton, IV et al. | |
| 2005/0267530 A1 | 12/2005 | Cummins | |
| 2006/0000868 A1 | 1/2006 | Shelton, IV et al. | |
| 2006/0015144 A1 | 1/2006 | Burbank et al. | |
| 2006/0022014 A1 | 2/2006 | Shelton, IV et al. | |
| 2006/0022015 A1 | 2/2006 | Shelton, IV et al. | |
| 2006/0025809 A1 | 2/2006 | Shelton, IV | |
| 2006/0025810 A1 | 2/2006 | Shelton, IV | |
| 2006/0025811 A1 | 2/2006 | Shelton, IV | |
| 2006/0025812 A1 | 2/2006 | Shelton, IV | |
| 2006/0025813 A1 | 2/2006 | Shelton, IV et al. | |
| 2006/0025816 A1 | 2/2006 | Shelton, IV | |
| 2006/0025817 A1 | 2/2006 | Ortiz et al. | |
| 2006/0039779 A1 | 2/2006 | Ringl | |
| 2006/0049230 A1 | 3/2006 | Shelton, IV et al. | |
| 2006/0085030 A1 | 4/2006 | Bettuchi | |
| 2006/0097026 A1 | 5/2006 | Shelton | |
| 2006/0124688 A1 | 6/2006 | Racenet et al. | |
| 2006/0163312 A1 | 7/2006 | Viola et al. | |
| 2006/0226196 A1 | 10/2006 | Hueil et al. | |

(56) References Cited

U.S. PATENT DOCUMENTS

| | | |
|---|---|---|
| 2006/0291981 A1 | 12/2006 | Viola et al. |
| 2007/0010838 A1 | 1/2007 | Shelton, IV et al. |
| 2007/0095877 A1 | 5/2007 | Racenet et al. |
| 2007/0131732 A1 | 6/2007 | Holsten et al. |
| 2007/0262116 A1 | 11/2007 | Hueil et al. |
| 2008/0078800 A1 | 4/2008 | Hess et al. |
| 2008/0078804 A1 | 4/2008 | Shelton et al. |
| 2008/0287989 A1* | 11/2008 | Weisel et al. ............ 606/220 |
| 2010/0137904 A1* | 6/2010 | Wenchell ............ 606/220 |
| 2010/0217314 A1* | 8/2010 | Holsten et al. ............ 606/220 |

FOREIGN PATENT DOCUMENTS

| | | |
|---|---|---|
| EP | 0169044 | 1/1986 |
| EP | 0 492 283 | 7/1992 |
| EP | 0588081 | 3/1994 |
| EP | 0878169 | 11/1998 |
| EP | 0640315 | 12/1998 |
| EP | 1090592 | 4/2001 |
| EP | 1316290 | 6/2003 |
| EP | 1479346 | 11/2004 |
| EP | 1607048 | 12/2005 |
| EP | 1 785 098 | 8/2006 |
| EP | 1728473 | 12/2006 |
| EP | 1 754 445 A2 | 2/2007 |
| EP | 1 875 868 | 1/2008 |
| EP | 1 917 918 | 5/2008 |
| EP | 2 095 777 | 9/2009 |
| FR | 2838952 | 10/2003 |
| GB | 2019296 | 10/1979 |
| GB | 2029754 A | 3/1980 |
| GB | 2051287 | 1/1981 |
| SU | 405234 | 9/1975 |
| SU | 1333319 | 8/1987 |
| SU | 1442191 | 12/1988 |
| SU | 1459659 | 2/1989 |
| WO | WO 86/02254 A1 | 4/1986 |
| WO | WO 90/05489 | 5/1990 |
| WO | WO 96/19146 A | 6/1996 |
| WO | WO 97/34533 | 9/1997 |
| WO | WO 02/30296 A | 4/2002 |
| WO | WO 03/094743 | 11/2003 |
| WO | WO 03/094747 | 11/2003 |
| WO | WO 2006/055385 A | 5/2006 |
| WO | WO 2008/007377 | 1/2008 |
| WO | WO2008/039250 | 4/2008 |
| WO | WO 2008/089050 | 7/2008 |

OTHER PUBLICATIONS

European Search Report EP08252283.0-1526 dated Jan. 26, 2009.
European Search Report EP09251224.3-2310 dated Oct. 8, 2009.
European Search Report EP09251268 dated Sep. 25, 2009.
European Search Report EP09251793.7 dated Nov. 16, 2009.
European Search Report EP10251797 dated Jan. 31, 2011.
European Search Report EP11004299.1269 dated Aug. 12, 2011.
European Search Report EP09251067 dated Mar. 9, 2011.
International Search Report from co-pending Int'l. Appln. No. PCT/US2008/062635 mailed Sep. 12, 2008.
International Search Report from EP Application No. 07 25 4366 dated Nov. 11, 2010.
International Search Report from EP Application No. 09 25 1067 mailed Mar. 17, 2011.
Extended European Search Report corresponding to EP 08 75 5056.2, dated Jul. 5, 2013; (9 pp).
Canadian Office Action issued in corresponding application No. 2891011 on Jun. 2, 2016.

\* cited by examiner

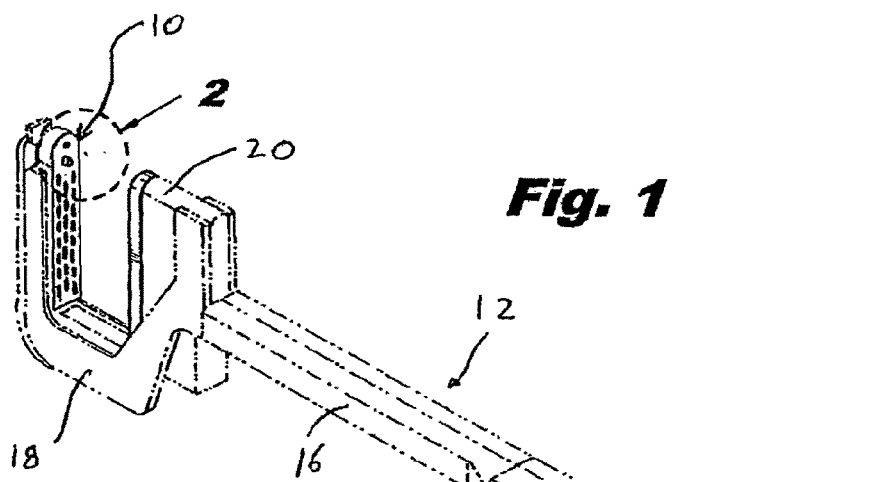
Fig. 1
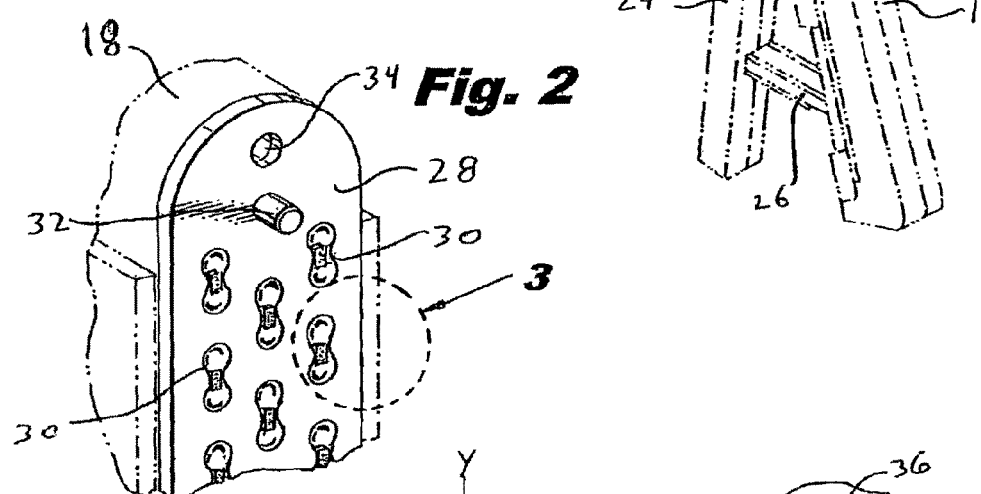
Fig. 2
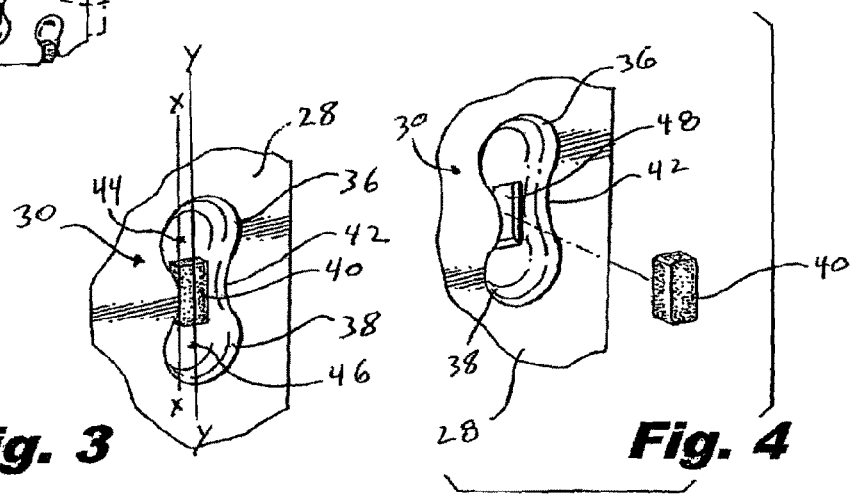
Fig. 3     Fig. 4

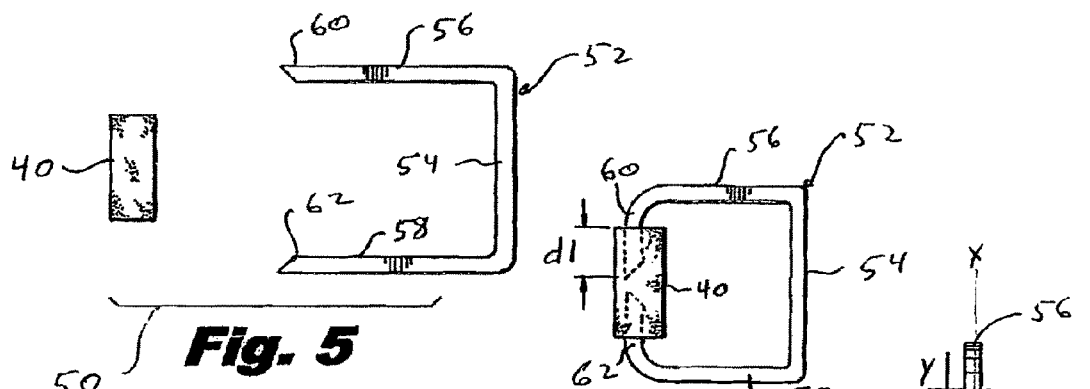
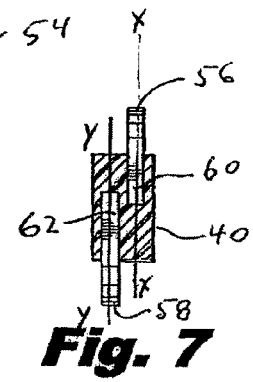
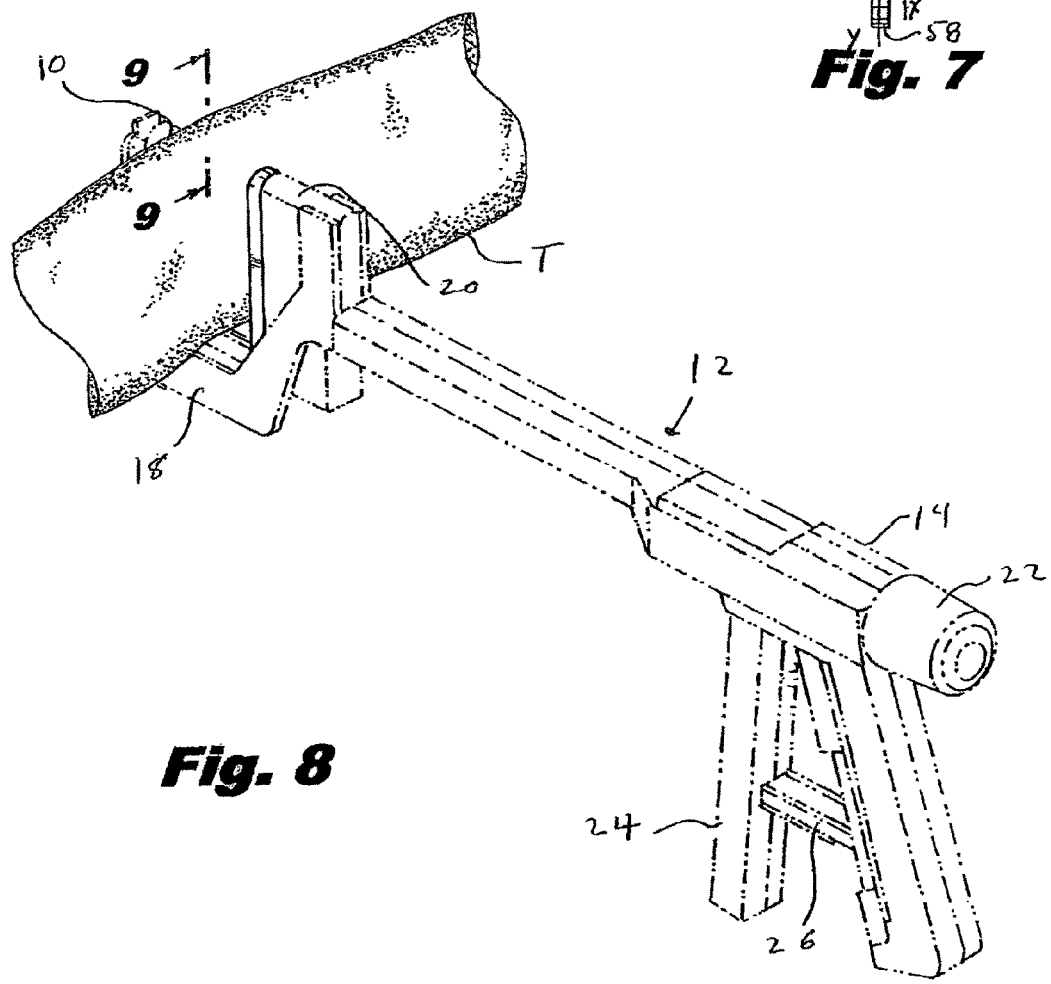

METHOD OF STAPLING TISSUES WITH A STAPLE ASSEMBLY

CROSS REFERENCE TO RELATED APPLICATIONS

This application is a National Stage Application of PCT/US2008/062635 filed May 5, 2008 under 35 USC §371(a), which claims priority of U.S. Provisional Application Ser. No. 60/928,244 filed on May 7, 2007, the entire contents of which are incorporated herein by reference.

BACKGROUND

Technical Field

The present disclosure relates to a variable size, uniform compression staple assembly and an associated anvil for use with a surgical stapling device. More particularly, the present disclosure relates to a two part, variable size, and uniform compression staple assembly for use with various thickness of tissue and an associated anvil for forming the staple assembly about the tissue.

Background of Related Art

Surgical stapling instruments or surgical staplers are used in many surgical operations to secure or join two or more tissue sections together. Some known surgical staplers are preloaded with a pre-chosen specific size staple for use in the surgical operations. However, the chosen staple is only capable of effectively sealing together a limited range of thicknesses of tissues. If the tissues are too thick for the chosen staple, the surgical stapler may not fully crimp the staple about the tissue resulting in the tissues pulling apart. Conversely, if the tissues are too thin for the chosen staple, the crimped or formed staple may not have enough compression to fully seal the tissues together resulting in leakage between the tissues. In other situations where the tissues are too thin for the chosen staple, the staple may be over crimped causing tissue penetrating tips of the staple to recurve back upon itself resulting in unnecessary puncturing of the tissues and again the possibility of leakage between the tissues.

Some surgical staplers are capable of accepting replaceable staple containing cartridges. Various ranges of different size staples may be provided by these cartridges for selection by a surgeon depending on the anticipated tissue thickness to be encountered. However, during a surgical operation, the surgical stapler needs to be removed from the operative site in order to replace one size staple cartridge with another when encountering differing thicknesses of tissues other than those anticipated.

Thus, it is desirable to provide a single size staple assembly capable of effectively stapling and sealing various thicknesses of tissue together. It is further desirable to provide an anvil for use with a surgical stapler and capable of securing components of a single size staple assembly together about tissue.

SUMMARY

There is provided a staple assembly for use with various thicknesses of tissues. The staple assembly includes a staple having a backspan and a pair of legs extending from the backspan. Each of the legs terminates in a tissue penetrating tip. The staple assembly further includes a staple block for receipt of the tissue penetrating tips such that the tissue penetrating tips lodge in the staple block upon being formed in a surgical stapler.

In one use of the disclosed staple assembly, the staple block receives the tissue penetrating tips along a common axis. In an alternative use of the staple assembly the staple block receives the tissue penetrating tips along parallel axes.

The staple and staple block of the staple assembly cooperate such that the tissue penetrating tips lodge into the staple block to a first depth upon passage through a first tissue having a first thickness. When formed about a second tissue having a second tissue thickness, the tissue penetrating tips lodge into the staple block to a second depth different from the first depth. The depth of penetration of the tissue penetrating tips into the staple block is inversely proportional to the tissue thickness encountered.

In one embodiment, the staple block is formed of a composite material. In alternative embodiments, the staple block is formed from materials such as, a plastic material, a polymeric material, an absorbable material, etc.

There is also provided an anvil for use with the disclosed two part staple assembly. The anvil includes an anvil plate having a first staple clinching pocket, a second staple clinching pocket spaced apart from the first staple clinching pocket and a recess for receipt of a component of a two part staple assembly. The recess is defined between the first and second staple clinching pockets.

In one embodiment, the recess is rectangular for receipt of a staple block of the staple assembly.

In one embodiment, the first staple clinching pocket lies along a first axis and the second staple clinching pocket lies along a second axis, wherein the second axis is parallel to the first axis. In another embodiment, the first and second axes lie along a common axis.

There is further provided a method of stapling tissues of differing thicknesses with a uniform size staple assembly. The method includes providing a surgical stapler having a staple head containing a staple and an anvil, the staple head and anvil being relatively movable. The anvil releasably contains a staple block. A tissue having a first thickness is captured between the staple head and the anvil. The staple is passed through the tissue such that tips of the staple lodge into the staple block to a depth inversely proportional to the first thickness of the tissue.

In one embodiment of the disclosed method, the tips of the staple pass into the staple block along parallel axes. In another embodiment of the disclosed method, the tips of the staple pass into the staple block along a common axis.

DESCRIPTION OF THE DRAWINGS

Various embodiments of the presently disclosed variable size, uniform compression staple assembly and associated anvil are disclosed herein with reference to the drawings, wherein:

FIG. 1 is a perspective view of one type of surgical stapling instrument incorporating one embodiment of an anvil and staple assembly;

FIG. 2 is an enlarged area of detail of FIG. 1 illustrating anvil and staple assembly components;

FIG. 3 is an enlarged area of detail of FIG. 2 illustrating a staple clinching pocket of the anvil and a staple block of the staple assembly;

FIG. 4 is perspective view, similar to FIG. 3, with the staple block separated from the staple pocket;

FIG. 5 is a side view of the staple assembly including the staple block and a uniform length staple;

FIG. 6 is a side view of the staple assembly of FIG. 5 formed and assembled;

FIG. 7 is a bottom view of an alternate configuration of the staple assembly in the formed and assembled condition;

FIG. 8 is a perspective view of the surgical stapling instrument of FIG. 1, positioned about a first tissue section;

DETAILED DESCRIPTION OF EMBODIMENTS

Figure 9:
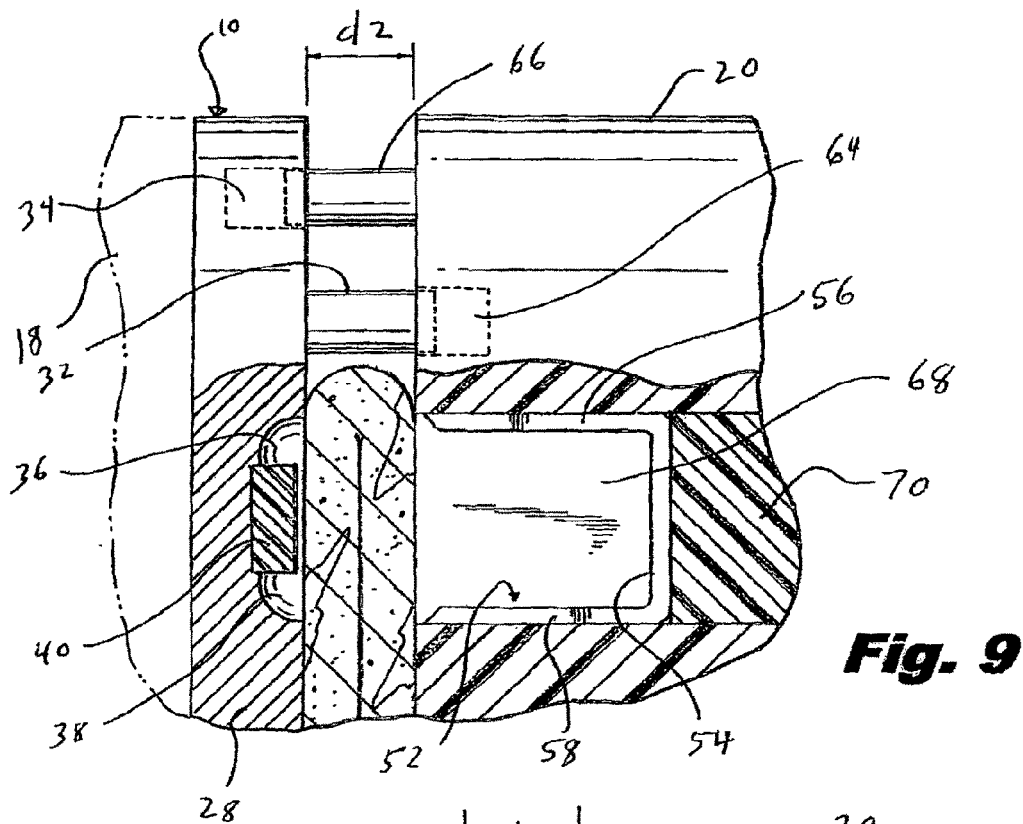
FIG. 9 is a side view, partially shown in section, of the tissue section captured between the anvil and a stapler head of the surgical stapling instrument.

Embodiments of the presently disclosed variable size, uniform compression staple assembly and associated anvil will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Referring initially to FIG. 1, there is disclosed an anvil 10 for use with a surgical stapler 12. Surgical stapler 12 is of a type typically used for open surgery procedures and includes a pistol grip handle 14 having an elongate member 16 extending distally from handle 14. Elongate member 16 terminates in a generally U-shaped anvil support 18. Anvil 10 is mounted on anvil support 18. Surgical stapler 12 also includes a staple containing head or staple head 20 which contains a plurality of uniform size staples as described in more detail hereinbelow. Staple head may be removable and replaceable. An adjustment knob 22 is provided on handle 14 and operates to move staple head 20 relative to anvil 10 in known manner in order to capture the tissue to be stapled therebetween. A trigger 24 is provided to actuate stapler 12 and eject a staple out of staple head 20, through tissue and into anvil 10.

Referring now to FIG. 2, anvil 10 includes an anvil plate 28 which is mounted to anvil support 18. Anvil plate 28 defines a plurality of staple forming pockets 30 which cooperate with staple head 20 to form, and support part of, a staple assembly. Anvil plate includes an alignment pin 32 and an alignment recess 34 which cooperate with a corresponding recess and pin on staple head 20 to ensure staples contained within staple head 20 are in proper alignment with staple forming pockets 30 during stapling of tissue.

With reference to FIG. 3, staple forming pocket 30 generally includes a first staple clinching depression or pocket 36 and a second staple clinching pocket 38 spaced apart from first staple clinching pocket 36. Pockets 36 and 38 are provided to receive tips of a staple and direct them toward a staple block 40 positioned in a narrowed central area 42 of staple forming pocket 30. A center point 44 of first staple clinching pocket 36 lies along an axis X-X while a center point 46 of second staple clinching pocket 38 lies along an axis Y-Y. In one embodiment, axis X-X is parallel to axis Y-Y. In an alternative embodiment, axis X-X is a common axis with axis Y-Y. The orientation of axis X-X relative to axis Y-Y determines how tips of a staple received within staple pockets 36 and 38, respectively, are guided into staple block 40 in a manner described in more detail hereinbelow.

As shown in FIG. 4, staple forming pocket 30 is provided with a rectangular recess 48 defined in narrowed central area 42. Recess 48 is provided to releasably retain staple block 40 within staple forming pocket 30. Staple block 40 may be retained in friction fit fashion or otherwise relasably held within recess 48 in staple forming pocket 30.

Referring now to FIG. 5, there is disclosed a novel, two part staple assembly 50 including staple block 40 and a staple 52 for use in stapling various thicknesses of tissue. By providing staple assembly with staple block 40, a single size staple 52 can be used to staple and effectively seal various thicknesses of tissues without having to change staple sizes as discussed herein. U-shaped staple 52 generally includes a backspan 54 and a pair of legs 56 and 58 extending from backspan 54. Legs 56 and 58 terminate in tissue penetrating tip sections 60 and 62, respectively.

As best shown in FIG. 6, when assembled, tip sections 60, 62 penetrate, and are lodged in, staple block 40. Staple block 40 may be formed from a variety of materials including composite, plastic or polymeric materials, absorbable materials, etc, or any other material capable of being penetrated by staple 52. Tip sections 60, 62 penetrate staple block 40 to a depth d1 which may vary depending on the thickness of tissue being stapled. Thus, staple block 40 is available to "take up" any excess length in legs 56 and 58 and allow a uniform or single size staple 52 to be used with various thicknesses of tissue. It should be noted that, while tip sections 60 and 62 are illustrated as entering staple block 40 substantially straight and parallel to the surfaces of rectangular staple block 40, in some instances tip sections 60 and 62 may be deformed or curved back toward backspan 54 slightly due to engagement with first and second staple clinching pockets 36 and 38, respectively.

As noted above, first and second clinching pockets 36 and 38, respectively, of staple forming pocket 30 are provided to direct tip sections 60, 62 into staple block 40. When axis X-X of first staple clinching pocket 36 lies along a common axis with axis Y-Y of second staple clinching pocket 38, tip sections 60,62 enter staple block 40 along a common axis.

Referring for the moment to FIG. 7, when staple forming pocket 30 is configured such that axis X-X of first staple clinching pocket 36 lies along a parallel but not common axis with axis Y-Y of second staple clinching pocket 38, tip sections 60, 62 enter staple block 40 on parallel but uncommon axes. In this embodiment of staple forming pocket 30, staple block 40 is capable of "taking up" an even greater amount of excess length in legs 56 and 58. Configuring staple forming pocket 30 in this manner is useful when a large range of tissue thicknesses are anticipated to be encountered during surgery.

It is also contemplated that the staple legs can enter the staple block on different non-parallel axes, with the anvil pockets formed to direct the legs in such manner.

Referring now to FIGS. 8-12, and initially with regard to FIG. 8, the use of staple assembly 50 and anvil 10, incorporated into surgical stapler 12 by way of example, to staple a tubular tissue T having a given thickness will now be described. It should be noted that, while the following discussion of the use of staple assembly 50 and anvil 10 is given in connection with one type of open surgery style surgical stapler 12, staple assembly 50 and anvil 10 find equal application when used in other types of open or minimally invasive surgical staplers, such as, for example, endoscopic or laparoscopic staplers, circular or anastomotic staplers, etc. Further, staple assembly 50 and anvil 10 are equally suited for use in stapling tissues other than tubular tissue sections.

Surgical stapler 12 is provided with a plurality of staples 52 loaded in staple head 20 in a manner discussed in more detail hereinbelow. Surgical stapler 12 is initially placed such that tissue section T is positioned between anvil 10 and staple head 20. Thereafter, adjustment knob 22 is manipulated to move staple head 20 toward anvil 10 and capture tissue T therebetween.

As shown in FIG. 9, captured tissue T has a thickness d2. Upon movement of staple head 20 toward anvil 10, alignment pin 32 on anvil plate 28 enters a recess 64 in staple head 20 and a staple head pin 66 on staple head 20 enters alignment recess 34 in anvil plate 28 to ensure proper alignment of staple legs 56 and 58 with staple clinching pockets 36 and 38, respectively. As noted above, staple head 20 is provided with a plurality of staples 52. Specifically, staples 52 are contained within staple pockets, such as staple pocket 68, formed in staple head 20. A pusher 70 is positioned within staple pocket 68 and is movable within staple pocket 68 in response to actuation of trigger 24 of surgical stapler 12. Movement of pusher 70 within staple pocket 68 causes pusher 70 to engage backspan 54 of staple 52 and drive staple 52 out of staple head 20 toward anvil 10.

Figure 10:
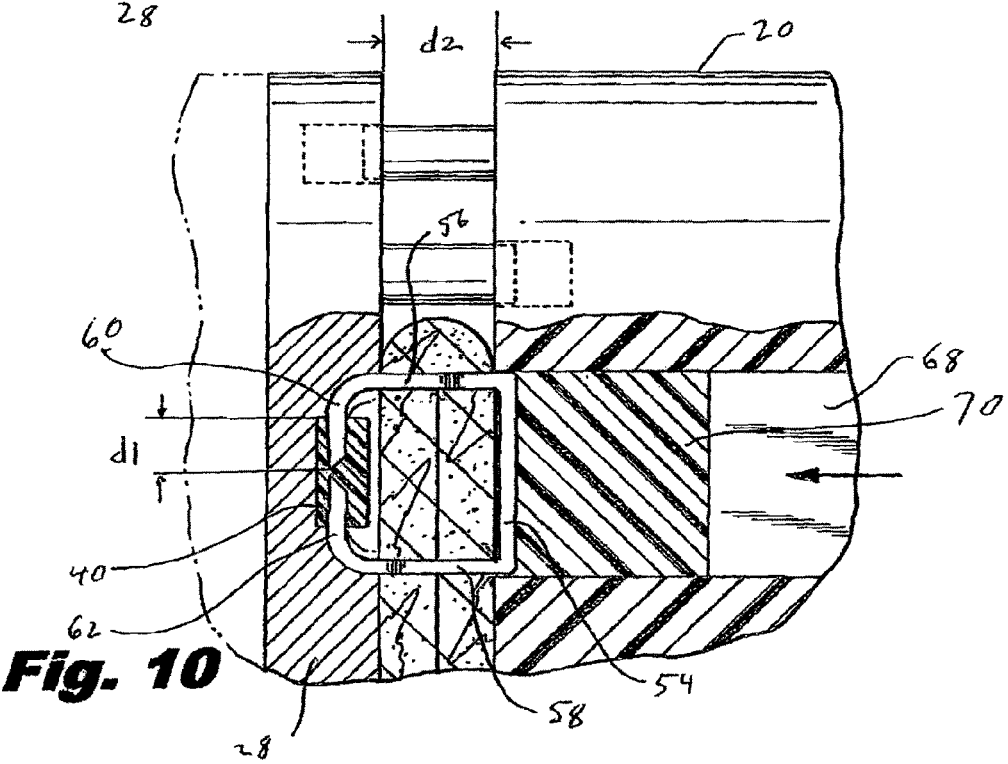
FIG. 10 is a side view, partially shown in section, illustrating the staple assembly formed through the tissue section.

Referring now to FIGS. 8 and 10, once surgical stapler 12 has been positioned about tissue T, lock lever 26 is disengaged from trigger 24 and trigger 24 is actuated (FIG. 8) to cause driver 70 to move distally within staple pocket 68 (FIG. 10). With continued reference to FIG. 10, pusher 70 drives staple 52 distally within staple pocket 68 such that tissue penetrating tip sections 60, 62 pass through tissue T. Upon engagement of tip sections 60, 62 with first and second staple clinching pockets 36 and 38, respectively, tip sections 60, 62 are clinched or deflected toward staple block 40 and penetrate tissue block 40 to depth d1. Tissue T is thus stapled between backspan 54 of staple 52 and staple block 40 and tip sections 60, 62. It should be noted that the depth d1 of penetration of tip sections 60, 62 into staple block 40 is inversely proportional to the thickness d2 of tissue T captured between anvil 10 and staple head 20 of surgical stapler 12. That is to say that the greater the thickness d2 of tissue t the less the depth d1 of penetration of tip sections 60, 62 into staple block 40. Tissue T is effectively sealed and stapled with staple assembly 50 without over or under penetration of staple 52.

Figure 11:
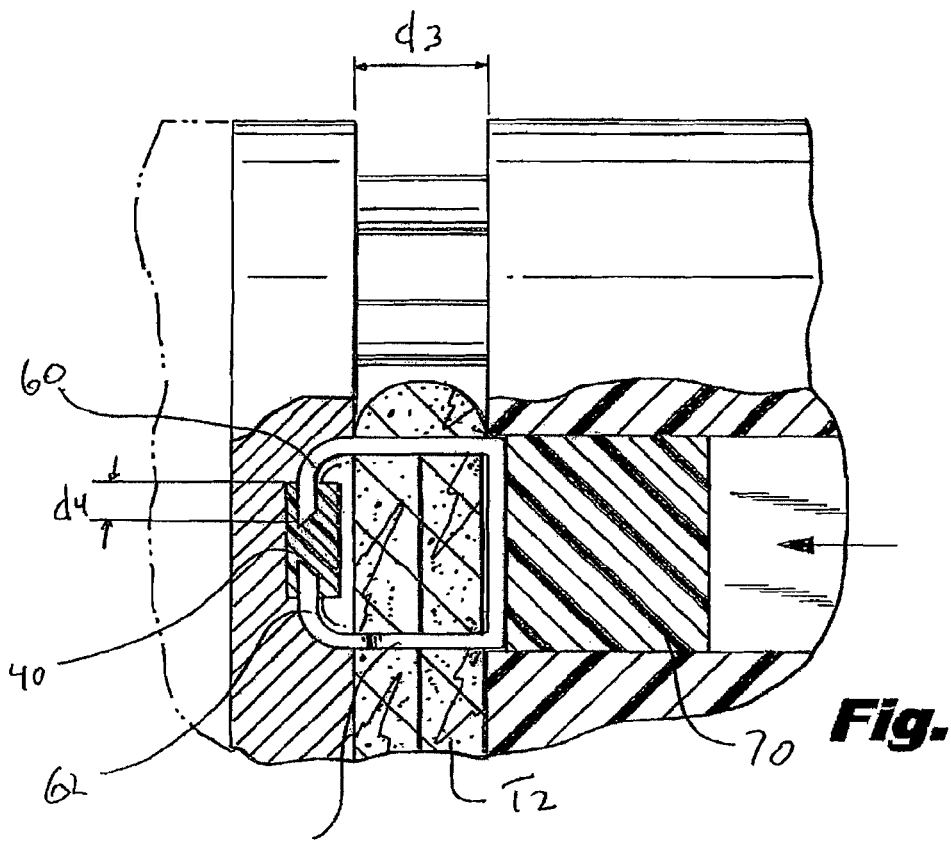
FIG. 11 is a view similar to FIG. 10 illustrating the staple assembly formed though a second tissue section having a thickness greater than the first tissue section.

Referring now to FIG. 11, staple assembly 50 is illustrated stapling an alternative tissue section T2 having a captured thickness d3 different from tissue thickness d2 described hereinabove. As shown, tip sections 60, 62 penetrate staple block 40 to a depth d4, which is inversely proportional to thickness d3, to effectively seal and staple tissue section T2 with staple assembly 50.

Figure 12:
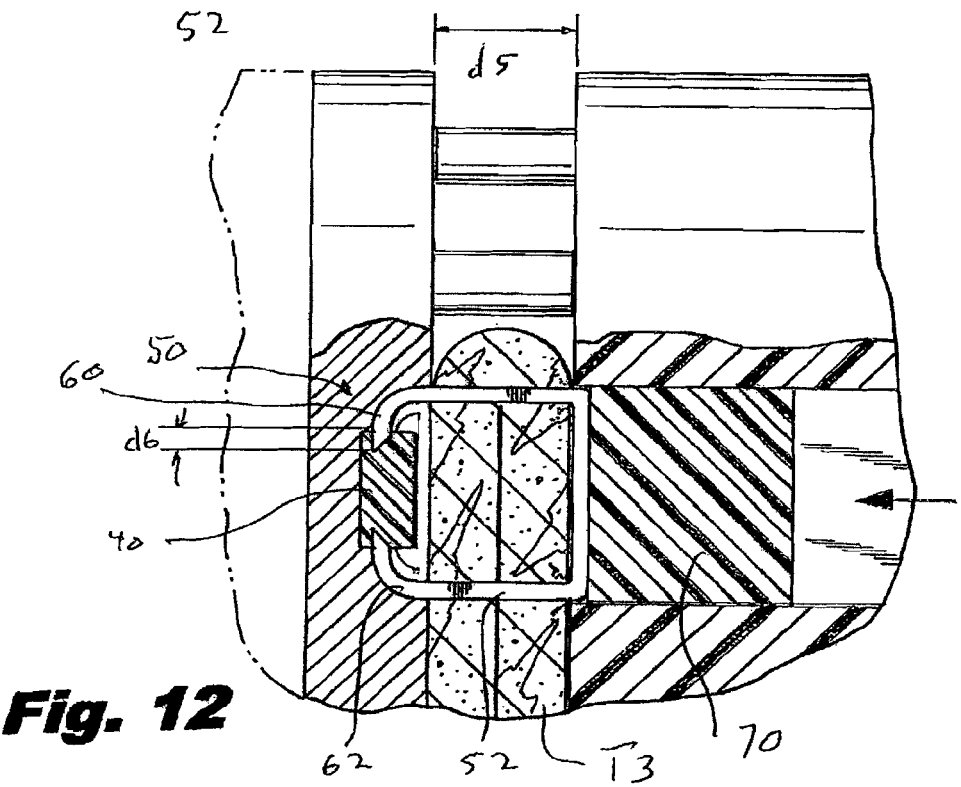
FIG. 12 is a view similar to FIG. 11 illustrating the staple assembly formed through a third tissue section having a thickness greater than the first and second tissue sections.

Referring further to FIG. 12, staple assembly 50 is illustrated stapling a further tissue section T3 having a captured tissue thickness d5 different from thickness d2 and d3 of tissue sections T and T2 described hereinabove (d5>d3>d2). Tip sections 60, 62 penetrate staple block 40 to a depth d6 which is inversely proportional to tissue thickness d5. Thus, it can be seen that staple assembly 50 in conjunction with anvil 10 is capable of stapling tissues of differing thickness utilizing only a single size staple 52 without over or under penetration of the subject tissue and attendant undesirable consequences.

It will be understood that various modifications may be made to the embodiments disclosed herein. For example, as noted above, the disclosed staple assembly and anvil configuration may find uses in other surgical stapling apparatuses than that shown. Also, although the stapling head is shown movable toward the anvil, the anvil could be movable instead, or both the anvil and staple head could be movable, to obtain the relative movement for approximation of the stapling head and anvil. Further, while the disclosed staple block and anvil pocket recess are shown as being rectangular, other shapes, such as round oval, triangular, etc. are contemplated herein to take up excess length of staple legs and provide a secure sealing and stapling of tissue. The staple block can be made up of a material which is loaded with or coated with a drug to aid in the healing of the tissue. Additionally, when used with a surgical stapling instrument capable of orienting the anvil at an angle relative to the staple head, the tips of the staple legs of specific staples within the staple head may enter their associated staple blocks to differing depths. Therefore, the above description should not be construed as limiting, but merely as exemplifications of particular embodiments. Those skilled in the art will envision other modifications within the scope and spirit of the claims appended hereto.

The invention claimed is:

1. A method of stapling tissues of differing thicknesses with a uniform size staple assembly comprising:
    providing a surgical stapler having a staple head containing a staple and an anvil, the anvil and staple head being relatively movable, the anvil releasably containing a staple block formed from a material and defining a rectangular configuration having a length, a width less than the length, and a height less than the length, the staple block including an exterior having four sides extending along the length of the staple block and opposed ends extending along the width of the staple block;
    capturing tissue having a thickness between the staple head and the anvil; and
    passing the staple through the captured tissue such that tips of the staple move toward one another along parallel axes to pierce the opposed ends of the exterior of the staple block, extend into the staple block, and lodge within the staple block at a depth proportional to the thickness and in a position wherein the tips are oriented in opposite directions in parallel orientation relative to the four sides of the staple block.

2. The method as recited in claim 1, wherein the material is a composite material.

3. The method as recited in claim 1, wherein the material is a plastic material.

4. The method as recited in claim 1, wherein the material is a polymeric material.

5. The method as recited in claim 1, wherein the material is an absorbable material.

* * * * *